United States Patent [19]

Kimura et al.

[11] Patent Number: 5,480,781

[45] Date of Patent: Jan. 2, 1996

[54] *BACILLUS* STRAINS FOR OXIDIZING HYDROXY GROUPS OF CHOLIC ACID AND CHENO DEOXYCHOLIC ACID TO KETO GROUPS

[75] Inventors: Hiromi Kimura, Koshigaya; Akio Okamura, Okegawa; Hiroshi Kawaide, Fujimi; Takurou Yamaura, Ashikaga, all of Japan

[73] Assignee: Tokyo Tanabe Company, Limited, Tokyo, Japan

[21] Appl. No.: 897,231

[22] Filed: Jun. 11, 1992

[30] Foreign Application Priority Data

Jun. 12, 1991 [JP] Japan ..................................... 3-236740
Jan. 27, 1992 [JP] Japan ..................................... 4-011598

[51] Int. Cl.$^6$ ............................. C12P 33/02; C12N 1/20
[52] U.S. Cl. ........................... 435/52; 435/61; 435/252.5; 435/147; 435/832
[58] Field of Search ........................... 435/52, 61, 252.5, 435/147, 832

[56] References Cited

U.S. PATENT DOCUMENTS 3,801,460   4/1974   Stoudt et al. .............................. 435/61

FOREIGN PATENT DOCUMENTS 5327786   3/1976   Japan .
5313708   8/1976   Japan .
6225356   7/1984   Japan .

OTHER PUBLICATIONS

Ann Microbiology Enzimology 38(2) 1988 pp. 249–256 (see abstract).

*Primary Examiner*—David M. Naff
*Assistant Examiner*—L. Blaine Lankford
*Attorney, Agent, or Firm*—McGlew and Tuttle

[57] ABSTRACT

Microorganisms from the genus Bacillus are used to convert chenodeoxycholic acid to 3-alpha-hydroxy-7-keto-5-beta-cholanic acid under aerobic conditions and alkaline pH. Preferred strains are Bacillus FERM BP-4390, Bacillus FERM BP-4391, Bacillus FERM BP-3651, Bacillus FERM BP-3393, Bacillus FERM BP-3398, Bacillus FERM BP-3395 and Bacillus FERM BP-3396. Microorganisms from the genus Bacillus are used to convert cholic acid to 3-alpha-hydroxy-7,12-diketo-5-beta-cholanic acid under aerobic conditions and alkaline pH. Preferred strains are Bacillus FERM BP-3393 and Bacillus FERM BP-3398. Microorganisms from the genus Bacillus are used to convert cholic acid to 3-alpha, 12-alpha-dihydroxy-7-keto-5-cholanic acid under aerobic conditions and alkaline PH. Preferred strains are Bacillus FERM BP-3395 and Bacillus FERM BP-4390.

7 Claims, No Drawings

BACILLUS STRAINS FOR OXIDIZING HYDROXY GROUPS OF CHOLIC ACID AND CHENO DEOXYCHOLIC ACID TO KETO GROUPS

BACKGROUND OF THE INVENTION

This invention relates to novel microorganisms having a conversion ability to bile acids and a position-specific oxidation method of the hydrocyl group of the di(or tri)-hydroxycholanic acid. More specifically, this invention relates to microorganisms having a conversion ability to bile acids and belonging to the genus Bacillus, and a method for preparing, using such a microorganism, 3α-hydroxy-7-keto-5-β-cholanic acid, or 3α, 12α-dihydroxy-7-keto-5-β-cholanic acid or 3α-hydroxy-7,12-diketo-5β-cholanic acid, each of which is an useful intermediate for preparation of 3α,7β-dihydroxy -5-β-cholanic aicd (hereinafter referred to as ursodeoxycholic acid) useful as a cholagogue, from 3α, 7α-dihydroxy-5-β-cholanic acid (hereinafter referred to as chenodeoxycholic acid) or 3α,7α,12α-trihydroxy-5β-cholanic acid (hereinafter referred to as cholic acid).

PRIOR ART

Heretofore, as a process of synthesizing ursodeoxycholic acid from chenodeoxycholic acid is known a process which comprises chemically converting the α-hydroxyl group at the 7-position of chenodeoxycholic acid to a β-hydroxyl group, namely a process which comprises selectively oxidizing the α-hydroxyl group at the 7-position of chenodeoxycholic acid to give 3α-hydroxy-7-keto-5β-cholanic acid and then stereoselectively reducing this 7-keto group to give ursodeoxycholic acid whose 7-position is a β-hydroxyl group.

Further, as a process of preparing 3α-hydroxy-7keto-5β-cholanic acid from chenodeoxycholic acid using a microorganism is known a process of using a microorganism belonging to the genus *Pseudomonas* (Japanese Puublished Examined Patent Application No. 25356/1987).

However, the chemically synthetic method, has problems in reactivity, selectivity and szfety on operation and were not satisfactory even in yield and the purity of resulting product.

Further, the above preparation process using a microorganism was not satisfactory because the concentration of chenodeoxycholic acid as a substrate is low and 1%, and its conversion is also low and 30.5%, and the process ws not satisfactory, either.

SUMMARY OF THE INVENTION

In the light of such present state of thins, the present inventors intensely studied about a process of preparation of 3α-hydroxy-7-keto- 5β-cholanic acid from chenodeoxycholic acid of high concentration as a substarate, and as a result they found that novel microorganisms belonging to the genus Bacillus produce 3α-hydroxy-7-keto- 5β-cholanic acid in high yield from chenodeoxycholic acid in high concentration as a substrate. These microorganisms were isolated from the soil in Yonezawa City, Yamagata Prefecture, and designated by the present inventors Bacillus sp. TTUR 2-2 (FERM BP–3651), Bacillus sp. TTUR 4-1 (FERM BP-4390) and Bacillus sp. TTUR 4-2 (FERM BP-4391).

A deposite of Bacillus sp. TTUR 2-2 (FERM BP-3651) was made on Nov. 22, 1990 in the International Depository: Fermentation Research Institute, Agency of Industrial Science and Technology, 1–3, Higashi 1 chome Tsukuba-shi Ibarak-ken, 305, Japan.

A deposite of each of Bacillus sp. TTUR 4-1 (FERM BP-4390) and Bacillus sp. TTUR 4-2 (FERM BP-4391) was made on Aug. 20, 1993 in said International Depository.

All these strains have an ability to oxidize the hydroxyl group(s) mainly at the 7-position of chenodeoxycholic acid to keto group(s) and at the same time have an, although weak, ability of oxidize the hydroxyl group at the 3-position to a keto group, but they do not exhibit a property to utilize or decompose the substrate chenodeoxycholic acid.

The present inventors furthe rproceeded with their study in order to obtain microorganisms capable of converting chenodeoxycholic acid as a substrate to 3α-hydroxy-7-keto-5β-cholanic acid in a further higher yield, and as a result they succeeded in separating mutant strains producing 3α-hydroxy-7-keto-5β-cholanic acid in a further higher yield (in a yield of 100% or nearly 100%, as later described) from chenodeoxycholic acid as a substrate by subjecting the above Bacillus sp. TTUR 2-2 to conventional mutation treatment, for example by irradiating it with ultraviolet ray, X-ray or Y rays or the like or by contacting it with a mutagenic agent such as N-methyl-N' -nitro-N-nitrosoguanidine, 4-nitroquinoline-N-oxide, acriflavine or ethyl methanesulfonate.

The following strais can be mentioned as such mutatn strains, a deposite of each of which was made on May 13, 1991 in the aforesaid International Depository.

(1) Bacillus sp. TTUR 2-M4 (FERM BP-3393)

(2) Bacillus sp. TTUR 2-M5 (FERM BP-3398)

(3) Bacillus sp. TTUR 2-M4-250 (FERM BP-3395) (4) Bacillus sp. TTUR 2-M4-294 (FERH BP-3396)

These mutant strains have an ability to produce 3α-hydroxy-7-keto- 5β-cholanic acid from chenodeoxycholic acid in a conversion of 100% or almost 100% and in a selectivity of 100% or almost 100% namely in a yield of 100% or almost 100%.

Namely, according to this invention is provided a process for preparing 3α-hydroxy-7-keto- 5β-cholanic acid which comprises culturing a microorganism belonging to the genus Bacillus and having an ability to convert chenodeoxycholic acid to 3α-hydroxy-7-keto- 5β-cholanic acid in a nutrient medium containing chenodeoxycholic acid, and recovering the produced 3α-hydroxy-7-keto- 5β-cholanic acid from the culture broth. Further, as microorganisms used in this case are provided, according to the invention the above-mentioned Bacillus sp. TTUR 2-2, Bacillus sp. TTUR 4-1, Bacillus sp. TTUR 4-2, Bacillus sp. TTUR 2-M4, Bacillus sp. TTUR 2-M5, Bacillus sp. TTUR 2-M4-250 and Bacillus sp. TTUR 2-M4-294.

Further, the present inventors cultured the above mutant strains using as a substrate cholic acid in place of chenodeoxycholic acid, and as a result they obtained as conversion products 3α-hydroxy-7,12 -diketo-5β-cholanic acid in case of the Bacillus sp. TTUR 2-M4 or Bacillus sp. TTUR 2-M5 and 3α, 12α-dihydroxy-7-keto- 5β-cholanic acid in case of the Bacillus sp. TTUR 2-M4-250 or Bacillus sp. TTUR 2-M4-294.

Thus, according to this invention is provided a process for preparing 3α-hydroxy-7,12-diketo-5β-cholanic acid which comprises culturing a microorganism belonging to the genus Bacillus and having an ability to convert cholic acid to 3α-hydroxy-7,12-diketo-5β-cholanic acid in a nutrient medium containing cholic acid, and recovering the produced 3α-hydroxy-7,12-diketo-5β-cholanic acid from the culture broth. Further, as microorganisms used in this case are provided, according to the invention the above-mentioned, Bacillus sp. TTUR 2-M4 or Bacillus sp. TTUR 2-M5.

Further, according to this invention is provided a process for preparing 3α, 12α-dihydroxy-7-keto-5β-cholanic acid which comprises culturing a microorganism belonging to the genus Bacillus and having an ability to convert cholic acid to 3α, 12α-dihydroxy-7-keto-5β-cholanic acid in a nutrient medium containing cholic acid, and recovering the produced 3α, 12α-dihydroxy-7-keto-5β-cholanic acid from the culture broth. Further, as microorganisms used in this case are provided, according to the invention, the above-mentioned Bacillus sp. TTUR 2-M4-250 or Bacillus sp. TTUR 2-M5-294.

DETAILED DESCRIPTION OF THE INVENTION

Separation of the wild strains Bacillus sp. TTUR 2-2, Bacillus sp. TTUR 4-1 and Bacillus sp. TTUR 4-2 from the soil were made according to the fol lowing methods.

A small amount of the soil was suspended in Horikoshi Medium I (1% glucose, 0.5% yeast extract, 0.1% dipotassium hydrogenphosphate, 0.02% magnesium sulfate heptahydrate, 1% sodium carbonate, pH10) containing 5% sodium cholate and subjected to enrichment culture at 30° C. for 5 days. One platinum loopful amount of the resulting culture broth was streak cultured on a Horikoshi Medium agar plate containing 5% sodium cholate and strains were purely separated. These strains were each cultured at 30° C. for 2 days in Horikoshi Medium I containing 5% sodium chenodeoxycholate, 3α-hydroxy-7-keto- 5β-cholanic acid in the culture broth was quantitatively determined, whereby strains were obtained having a highconversion ability to 3α-hydroxy-7-keto-5β-cholanic acid.

The bacteriological characteristics of these strains are shown in the following Tables 1 to 8. These tests and classification were carried out according to "BERGEY'S MANUAL of Systematic Bacteriology", and in the respective tests were used media adjusted to pH 10 by addition of sodium carbonate unless otherwise noted.

From the above investigation results, it is apparent that the TTUR 2-2, TTUR 4-1, and TTUR 4-2 strains are microorganisms belonging to the genus Bacillus because they are aerobic sporogenous bacteria. However, they are different from general microorganisms of the genus Bacillus in point that their optimum pH values for growth are in an alkali side around 10.

Further, when these strains were compared with respective type strains of *Bacillus alcalophilus* and *Bacillus alcalophilus* subsp. *halodurans,* the former strains Here remarkably different from the latter strains in the shape of colony and the appearance of the peripheral portion of colony.

*Bacillus cereus* 8-1 (FERM P-2885, Japanese Published Examined Patent Application No.13708/1978 ) and *Bacillus alcalophilus* 202-1 (FERM P-2674, Japanese Published Examined Patent Application No.27786/1978 ) were reported as alkalophilic strains wherein their colonies were irregular in an alkaline atmosphere and the periphery of the colonies was lobate, but the present strains are yet different from these strains in characteristics.

In Table 9 were shown the main characteristics of the TTUR 2-2, TTUR 4-1 and TTUR 4-2 strains, and in Table 10 the main characteristics of *Bacillus alcalophilus, Bacillus alcalophilus* subsp. *halodurans, Bacillus cereus* 8-1 and *Bacillus alcalophilus* 202-1.

Therefore, although the TTUR 2-2 and TTUR 4-1 and TTUR 4-2 strains are aerobic sporogenous bacteria, they are distinguished from known species belonging to the genus Bacillus, as stated above, in various bacteriological characteristics, particularly in that the optimum pH for growth exists in the alkali side-around 10, and in that these strains have an ability to convert chenodeoxycholic acid to 3α-hydroxy- 7-keto-5β-cholanic acid. Thus, it is suitable to acknowledge these strains as novel species.

A specific method for obtaining mutant strains Bacillus sp. TTUR 2-M4, Bacillus sp. TTUR 2-M5, Bacillus sp. TTUR 2-M4-250 and Bacillus sp. TTUR 2-M4-294 is exhibited in the later-described example. Further, The bacteriological properties of the above mutant strains were shown in Tables 11 to 20, together with the bacteriological properties of their parent strain Bacillus sp. TTUR 2-2 for reference.

As is the case with the parent strain, the tests in the tables and classification were carried out according to "BERGEY'S MANUAL OF Systematic Bacteriology", and in the respective tests were used media adjusted to pH 10 by addition of sodium carbonate unless otherwise noted.

Since mutant strains are considered in general to belong to the same species as their parent strains belong to, it was concluded that all the mutant strains of Bacillus sp. TTUR 2-2 belong to the same novel species. Thus, the mutant strains of the invention are not limited to Bacillus sp. TTUR 2-M4, TTUR 2-M5- and TTUR 2-M4-250 and TTUR 2-M4-294, and include any strains which belong to the genus Bacillus and produce 3α-hydroxy-7-keto-5β-cholanic acid using chenodeoxycholic acid as a substrate, and any strains which belong to the genus Bacillus and produce either 3α-hydroxy-7,12-diketo-5β-cholanic acid or 3α, 12α-dihydroxy-7-keto- 5β-cholanic acid using cholic acid as a substrate.

According to this invention, 3α-hydroxy-7-keto-5β-cholanic acid can be produced by culturing a microorganism belonging to the genus Bacillus and capable of converting chenodeoxycholic acid to 3α-hydroxy- 7-keto-5β-cholanic acid in a nutrient medium containing chenodeoxycho acid.

Further, according to this invention, 3α-hydroxy-7,12-diketo-5β-cholanic acid can be produced by culturing a mutant strain belonging to the genus Bacillus and capable of converting cholic acid to 3α-hydroxy- 7,12-diketo-5β-cholanic acid in a nutrient medium containing cholic acid.

Further, according to this invention, 3α, 12α-dihydroxy-7-keto-- 5β-cholanic acid can be produced by culturing a mutant strain belonging to the genus Bacillus and capable of converting cholic acid to 3α, 12α-dihydroxy-7-keto-5β-cholanic acid in a nutrient medium containing cholic acid.

Although there is no particular limitation about the concentration of the substrate in the nutrient medium, namely chenodeoxycholic acid, or cholic acid, it is suitable in view of the yield of the desired conversion product and culture conditions, that the concentration is in the range of 5 to 500 g/l, preferable 40 to 300 g/l.

Any media can be used in this invention so long as the microorganisms used in the invention can proliferate thetin, and, for example, there can be used as carbon sources various saccharide raw materials such as glucose, fructose, sucrose, glycerol, starch, bran and blackstrap molasses, and as nitrogen sources organic nitrogencontaining substances such as peptone, meat extract, yeast extract, corn steep liquor, soybean meal, rapeseed oil cake, urea, various amino acids and amino-sugars, and inorganic nitrogen compounds such as ammonium nitrate, ammonium chloride and sodium nitrate. Further, it is preferred to further add very small amounts of inorganic metal salts, vitamins, growth promoting factors, etc.

Culture in the process of the invention can be carried out under an aerobic condition, for example by an aeration stirring culture method or reciprocal shaking method. Culture conditions are not particularly limited, but in general a temperature of 20° to 40° C., a pH of 7 to 11 and a culture time of the order of 1 to 6 days. When culture is carried out at a high alkaline pH, for example at a pH of 10, the fear of contamination with various germs during cuture is diminished, and the operation of sterilization of media usually carried out can be omitted. Of course, even in such a case, there is no hindrance in carrying out sterilization operation.

In recovering the desired conversion product, namely, 3α-hydroxy-7-keto-5β-cholanic acid, 3α-hydroxy-7,12-diketo-5β-cholanic acid or 3α, 12α-dihydroxy-7-keto-5β-cholanic acid from the culture broth, first, the microorganism and insoluble matters in the culture broth are removed by filtration, centrifugation or the like, and the resulting culture Filtrate or supernatant was acidified by addition of hydrochloric acid or gulfuric acid. By this, the formed conversion product precipitates in a good yield. Then, this precipitate is separated by filtration and tration and recrystallized, and thereby the conversion product can be recovered in a highly pure state.

Any of these conversion products can be converted to ursodeoxycholic acid by further subjecting it to microorganism conversion alone or in combination with chemial reaction(s).

This invention is further described below according to examples, but it goes without saying that the invention is not limited to these examples.

In each example, products were identified by thin layer chromatography or high performance liquid chromatography under the following conditions, respectively.

(1) Thin layer chromatography Carrier; Kieselgel 60 (0.25mm thick, produced by Herck Co.) Developing solvent;

(1) Benzene/isopropyl alcohol/acetic acid (40/10/1, volume ratio)

(2) Chloroform/acetone/acetic acid (7/2/1, volume ratio)

Coloring; An phosphomolybdic acid-sulfuric acid reagent (obtained by dissolving 1 g of phosphomolybdic acid in 20 ml of methanol and adding 1 ml of concentrated sulfuric acid ) is sprayed, and the resulting carrier is subjected to coloring with heating until the bile acid spot becomes deep blue.

Charge volume of a sample; 1 μl of the culture broth (2) High performance liquid chromatography (1) Column; Capcell Pak C18 (type AG 120, S-5 μm, column size 4.6Φ ×150 mm, produced by Shiseido. Co., Ltd.)

Moving phase; methanol/purified watier/phosphoric acid (70/30/0.02 M, weight ratio)

Flow rate; 1.7 ml/min (2) Column; Inertcil ODS column (column size 4.6Φ×250 mm, produced by GL Sc i ence Co.)

Moving phase; methanol/purified water/phosphoric acid (70/30/0.02 M, weight ratio )

Flow rate; 1.0 ml/min

Detection; RI

Identification of peak; compared with a standard substance

The mutant strains were separated by the following methods.

(1) Bacillus sp. TTUR2-M4 and Bacillus sp. TTUR 2-M5

One platinum loopful of Bacillus sp. TTUR 2-2 grown on a slant of an alkaline NA medium (composition: 1.8% nutrient broth "Eiken" (trade name, produced by Eiken Chemical Co., Ltd.), 1.8% agar, 0.75% sodium carbonate, pH10) was inoculated into 20 ml of Horikoshi Medium I (composition: 1% glucose, 0.5% peptone, 0.5% yeast extract, 0.1% dipotassium hydrogenphosphate, 0.02% magnesium sulfate heptahydrate, 1% sodium carbonate, pH-10) in a test tube (30Φ×190 mm), and cultured with shaking at 30° C. for 16 hours.

Then, the above cells during the logarithmic phase were aseptically collected by centrifugation, and washed three times with 10 ml of a 0.1M Trig-maleate buffer (pH 8,0). The cells after washing were suspended in 25 ml of the same buffer, N-methyl-N'-nitro-N-nitrosoguanidine (hereinafter referred to as NTG) was added so that its final concentration became 60 μg/ml, and the cells were incubated at 30° C. for 30 minutes to conduct mutation treatment. The death rate of Bacillus sp. TTUR 2-2 was 85% under this treatment condition.

Then, 1 ml of this cell suspension was taken and immediately diluted with 9 ml of a 0.1M sodium carbonate buffer (pH 9.5), and the cells were collected by centrifugation. hfter the same washing operation using the above buffer was repeated twice, the resulting cells were suspended in 10 ml of an alkaline NB medium (composition: 1.8% nutrient broth "Eiken", 0.75% sodium carbonate, pH 10). The cell suspension was appropriately diluted with the alkaline NB medium, applied onto the alkaline NA plate medium so that 10 to 100 colonies could emerge, and cultured at 30° C. for 2 days.

Among the emerged colonies, those growing after the 2 days and having a medium colony size were isolated, transplanted on a slant of a 5% CA agar medium (pH 10, obtained by adding 5% cholic acid, 0.5% sodium hydroxide and 1.8% agar to Horikoshi Medium I), and cultured at 30° C. for 3 days. Sufficiently grown strains were selected, and one loopful portions of the strains were inoculated into 4 ml portions of a 5% CA liquid medium (pH 10, comprising the 5% CA agar medium from which agar was removed) in test tubes (16.5Φ×165mm), respectively, and cultured with shaking at 30° C. for 3 days. Conversion products in the resulting respective culture broths were investigated by thin layer chromatography, and thereby mutant strains (Bacillus sp. TTUR 2-M4 and Bacillus sp. TTUR 2-M5) were found both of which completely lacked an ability to convert the hydroxyl group at the 3-position of cholic acid to a keto group. llereinafter, the above method of obtaining a mutant strain is merely referred to as the NTG treatment.

(2) Bacillus sp. TTUR 2-M4-250 and Bacillus sp. TTUR 2-M4-294

The NTG treatment was repeated using as a parent strain Bacillus sp. TTUR 2-M4 obtained by the NTG treatment of (1), except that the 5% CA liquid medium was used as a starting medium for cell proliferation. An MTG concentration of 60 μg/ml was adopted at the time of NTG treatment. As a result, mutant strains (Bacillus sp. TTUR 2-M4-250 and Bacillus sp. TTUR 2-M4-294) were found both of which completely lacked an ability to convert the hydroxyl groups at the 3- and 12- positions of cholic acid to keto groups, respectively. The death rate of Bacillus sp. TTUR 2-M4 was 15% in this operation.

The mutant strains obtained by the NTG treatments of (1) and (2) were cultured with shaking at 30° C. for 3 days in 4 ml portions of Horikoshi Medium I containing 5% cheno deoxycholic acid in test tubes (16.5Φ×165 mm), and the resulting conversion product was investigated by thin layer chromatography, and thereby specific production of the desired 3α-hydroxy-7-keto- 5β-cholanic acid was confirmed.

EXAMPLE 1

Bacillus sp. TTUR 2-2 (FERM BP-3651) was cultured according to the method shown below. 10 g of glucose, 5 g of peptone, 5 g of yeast extract, 1 g of dipotassium hydrogenphosphate and 0.2 g of magnesium sulfate heptahydrate were dissolved in 500 ml of purified water. Separately, 50 g of chenodeoxycholic acid, 5 g of sodium hydroxide and 10 of sodium carbonate were dissolved in 500 ml of purified water. Both solutions were sterilized at 121° C. for 15 minutes and, after cooling, were mixed to give a medium (pH 10).

20 ml of this medium was put in a test tube (3Φ×19 cm), 0.1 ml of a culture broth was aseptically inoculated therein which had been obtained by culturing the strain at 30° C. for 20 hours in 20 ml of a medium in a test tube having the same composition as in the above medium except that chenodeoxycholic acid and sodium hydroxide were excluded. Thereafter, the strain was cultured with shaking at 30° C. for 2 days. After the culture, the cells were removed by centrifugation, and the culture supernatant was acidified with dilute gulfuric acid to precipitate 3α-hydroxy-7-keto-5β-cholanic acid and nonconverted chenodeoxycholic acid. This precipitate was collected and dried to obtain 0.98 g of white powder. Part of the powder was taken and subjected to high performance liquid chromatography to determine the production ratio of chenodeoxycholic acid, 3α-hydroxy-7-keto-5β-cholanic acid, and other chenodeoxycholic acid oxidation products (hereinafter referred to as "other bile acids"). As a result, the production ratio was 2.8% of chenodeoxycholic acid, 85.9% of 3α-hydroxy- 7-keto-5β-cholanic acid and 11.3% of other bile acids. This mixture was subjected to recrystallization from methanol to obtain pure 3α-hydroxy-7-keto-5β-cholanic acid.

EXAMPLE 2

The procedure of Example 1 was repeated except that Bacillus sp. TTUR 4-1 (FERM BP-4390) was substituted for the strain of Example 1. The determined production ratio was 1.6% of chenodeoxycholic acid, 75.3 % of 3α-hydroxy-7-keto-5β-cholanic acid and 23.1% of other bile acids.

EXAMPLE 3

The procedure of Example 1 was repeated except that Bacillus sp. TTUR 4-2 (FERM BP-4391) was substituted for the strain of Example 1. The determined production ratio was 0% of chenodeoxycholic acid, 87.7% of 3α-hydroxy-7-keto-5β-cholanic acid and 12.3% of other bile acids.

EXAMPLE 4

10 g of glucose, 5 g of peptone., 5 g of yeast extract, 1 g of dipotassium hydrogenphosphate and 0.2 g of magnesium sulfate heptahydrate were dissolved in 500 ml of purified water. Separately, 100 g of chenodeoxycholic acid, 10 g of sodium hydroxide and 10 g of sodium carbonate were dissolved in 500 ml of purified water. Both solutions were sterilized at 121° C. for 15 minutes and, after cooling, were mixed to give a medium (pH 10).

100ml of this medium was put in a Sakaguchi flask (volume:500 ml), 0.1 ml of a culture broth was aseptically inoculated therein which had been obtained by culturing Bacillus sp. TTUR 2-2 at 30° C. for 20 hours in 20 ml of a medium in a test tube (3Φ×19 cm) having the same composition as in the above medium except that chenodeoxycholic acid and sodium hydroxide were excluded. Thereafter, the strain was cultured with shaking at 30° C. for 4 days.

The resulting culture broth was, then, treated in the same manner as in Example 1 to obtain 3 α-hydroxy-7-keto-5β-cholanic acid. The production ratio was 4.2% of chenodeoxycholic acid, 88.5% of 3α-hydroxy- 7-keto-5β-cholanic acid and 7.3% of other bile acids.

EXAMPLE 5

The procedure of Example 2 was repeated except that the use amount of sodium hydroxide in Example 2 was changed to 7 g (pH 10.5). The determined production ratio was 4.2% of chenodeoxycholic acid, 85.9% of 3α-hydroxy-7-keto-5β-cholanic acid and 9.9% of other bile acids.

EXAMPLE 6

The procedure of Example 3 was repeated except that the use amount of chenodeoxycholic acid and sodium hydroxide were changed to 150 g and 15 g, respectively and the number of days of culture was changed to 4 days in Example 3. The determined production ratio was 22.2% of chenodeoxycholic acid, 65.3% of 3α-hydroxy-7-keto-5β-cholanic acid and 12.5% of other bile acids.

EXAMPLE 7

Bacillus sp. TTUR 2-M4 (FERM BP-3393) was cultured according to the following method. 10 g of glucose, 5 g of peptone, 5 g of yeast extract, 1 g of dipotassium hydrogenphosphate and 0.2 g of magnesium sulfate heptahydrate were dissolved in 500 ml of purified water. Separately, 50 g of chenodeoxycholic acid, 5 g of sodium hydroxide and log of sodium carbonate were dissolved in 500 ml of purified water. Both solutions were sterilized at 121° C. for 15 minutes and, after cooling, were mixed to give a medium (pH 10).

20 ml of this medium was put in a test tube (3Φ×19 cm), and 0.1 ml of a culture broth was aseptically inoculated therein which had been obtained by culturing with shaking the strain at 30° C. overnight in 20 ml of a medium in a test tube having the same composition as in the above medium except that chenodeoxycholic acid and sodium hydroxide were excluded. Thereafter, the strain was cultured with shaking at 30° C. for 3 days.

After the culture, the cells were removed by centrifugation, the resulting culture supernatant was acidified with dilute sulfuric acid to form a precipitate. This precipitate was collected and dried to obtain 0.999 g of white powder. Part of this precipitate was taken and subjected to high performance liquid chromatography to determine the production ratio of chenodeoxychol ic acid and 3α-hydroxy-7-keto-5β-cholanic acid. The production ratio was 0% of chenodeoxycholic acid, and 100% of 3α-hydroxy-7-keto-5β-cholanic acid (recovery 99.9%).

EXAMPLE 8

The procedure of Example 7 was repeated except that Bacillus sp. TTUR 2-M5 (FERM BP-3398) was substituted for the strain of Example 7. The production ratio was 0% of chenodeoxycholic acid and 100% of 3α-hydroxy- 7-keto-5β-cholanic acid (recovery 99.9).

EXAMPLE 9

The procedure of Example 7 was repeated except that Bacillus sp. TTUR 2-M4-250 (FERM BP-3395) substituted for the strain of Example 7. The production ratio was 0% of chenodeoxycholic acid and 100% of 3α-hydroxy- 7-keto-5β-cholanic acid (recovery 99.9%).

EXAMPLE 10

The procedure of Example 7 was repeated except that Bacillus sp. TTUR 2-M4-294 (FERN BP-3396) substituted for the strain of Example 7. The production ratio was 1.4% of chenodeoxycholic acid and 98.6% of 3α-hydroxy-7-keto-5β-cholanic acid (recovery 99.9%).

EXAMPLE 11

The procedure of Example 7 was repeated except that a medium (pH 10) comprising the medium of Example 7 from which glucose was excluded was used. The production ratio was 0% of chenodeoxycholic acid and 100 % of 3α-hydroxy-7-keto-5β-cholanic acid.

EXAMPLE 12

The procedure of Example 10 was repeated except that a medium (pH 10) comprising the medium of Example 10 from which glucose was excluded was used. The production ratio was 0% of chenodeoxycholic acid, and 100% of 3α-hydroxy-7-keto-5β-cholanic acid.

EXAMPLE 13

Bacillus sp. TTUR 2-M5 was cultured by the following method. 5 g of yeast extract, 1 g of dipotassium hydrogenphosphate and 0.2 g of magnesium gulfate heptahydrate were dissolved in 500 ml of purified water. Separately, 50 g of chenodeoxycholic acid, 5 g of sodium hydroxide and 4 g of sodium carbonate were dissolved in 500 ml of purified water. Both solutions were sterilized at 121° C. for 15 minutes and, after cooling, were mixed to give a medium (pH 9.7).

Thereafter, the procedure of Example 8 was repeated. The production ratio was 0% of chenodeoxycholic acid and 100% of 3 α-hydroxy-7-keto- 5β-cholanic acid.

EXAMPLE 14

The procedure of Example 13 was repeated except that Bacillus sp. TTUR 2-M4-250 was used as a strain. The production ratio was 0% of chenodeoxycholic acid and 100% of 3α-hydroxy-7-keto-5β-cholanic acid.

EXAMPLE 15

Bacillus sp. TTUR 2-M4 was cultured by the following method. 10 g of soybean protein (Ajipron E3; trade name, produced by Ajinomoto Co., Ltd.), 1 g of dipotassium hydrogenphosphate and 0.2 g of magnesium sulfate heptahydrate eere dissolved in 500 ml of purified water. Separately, 50 g of chenodeoxycholic acid, 5 g of sodium hydroxide and 2 g of sodium carbonate were dissolved in 500 ml of purified water. Both solutions were sterilized at 121° C. for 15 minutes and, after cooling, were mixed to give a medium (pH 10.2).

Thereafter, the procedure of Example 7 was repeated. The production ratio was 0% of chenodeoxycholic acid and 100% of 3α-hydroxy- 7-keto-5β-cholanic acid.

EXAMPLE 16

The procedure of Example 15 was repeated except that Bacillus sp. TTUR 2-M5 was used as a strain. The production ratio was 0% of chenodeoxycholic acid and 100% of 3α-hydroxy-7-keto-5β-cholanic acid.

EXAMPLE 17

Bacillus sp. TTUR 2-M5 was cultured by the following method. 10 g of glucose, 5 g of peptone, 5 g of yeast extract, 1 g of dipotassium hydrogenphosphate and 0.2 g of magnesium sulfate heptahydrate were dissolved in 500 ml of purified water. Separately, 100 g of chenodeoxycholic acid, 10 g of sodium hydroxide and 10 g of sodium carbonate were dissolved in 500 ml of purified water. Both solutions were sterilized at 121° C. for 15 minutes and, after cooling, were mixed to give a medium (pH 10). 100 ml of this medium was put in a Sakaguchi flask (volume:500 ml), and 2 ml of a culture broth was aseptically inoculated therein which had been obtained by culturing the strain at 30° C. for 48 hours in 2 ml of a medium in a test tube (3Φ×19 cm) having the same composition as in the above medium. Thereafter, the strain was cultured with shaking at 30° C. for 6 days.

Thereafter, the same procedure as in Example 8 was repeated. The production ratio was 5.8% of chenodeoxycholic acid and 94.2% of 3α-hydroxy- 7-keto-5β-cholanic acid.

EXAMPLE 18

Bacillus sp. TTUR 2-M4 was cultured by the following method. 10 g of glucose, 5 g of peptone, 5 g of yeast extract, 1 g of dipotassium hydrogenphosphate and 0.2 g of magnesium gulfate heptahydrate were dissolved in 500 ml of purified water. Separately, 50 g of cholic acid, 5 g of sodium hydroxide and 10 g of sodium carbonate were dissolved in 500 ml of purified water. Both solutions were sterilized at 121° C. for 15 minutes and, after cooling, were mixed to give a medium (pH 10).

20 ml of this medium was put in a test tube (3Φ×19 cm), and 0.1 ml of a culture broth was aseptically inoculated therein which had been obtained by culturing the strain at 30° C. overnight in 20 ml of a medium in a test tube having the same composition as in the above medium except that cholic acid and sodium hydroxide were excluded. Thereafter, the strain was cultured with shaking at 30° C. for 3 days.

Thereafter, the procedure of Example 7 was repeated to determine the production ratio of cholic acid and 3α-hydroxy-7,12-diketo-5β-cholanic acid. The ratio was 0% of cholic acid and 100% of 3α-hydroxy- 7,12-diketo-5β-cholanic acid (recovery 99.7%).

EXAMPLE 19

The procedure of Example 18 was repeated except that Bacillus sp. TTUR 2-M5 was used as a strain and the number of days of culture of 2 days was adopted. The production ratio was 0% of cholic acid and, 98.2% of 3α-hydroxy-7,12-diketo-5β-cholanic acid, 1.4% of 3α, 12α-dihydroxy- 7-keto-5β-cholanic acid and 0.3% of 3α,7α-dihydroxy-12-keto- 5β-cholanic acid (recovery 99.6%).

EXAMPLE 20

The procedure of Example 18 was repeated except that Bacillus sp. TTUR 2-M4-250 was used as a strain. The production ratio was 0% of cholic acid and 100% of 3α, 12α-dihydroxy-7-keto-5β-cholanic acid.

EXAMPLE 21

The procedure of Example 18 was repeated except that Bacillus sp. TTUR 2-M4-294 was used as a strain. The production ratio was 0.8% of cholic acid and 99.2% of 3α, 12α-dihydroxy-7-keto-5β-cholanic acid.

EXAMPLE 22

The procedure of Example 19 was repeated except that a medium (pH 10) comprising the medium of Example 19 from which glucose was excluded was used. The production ratio was 0% of cholic acid and 100% of 3α, 12α-dihydroxy-7-keto- 5β-cholanic acid.

EXAMPLE 23

The procedure of Example 21 was repeated except that a medium (pH 10) comprising the medium of Example 21 from which glucose was excluded was used. The production ratio was 0% of cholic acid and 100% of 3α, 12α-dihydroxy-7-keto-5β-cholanic acid.

EXAMPLE 24

Bacillus sp. TTUR 2-M4 was cultured by the following method. 10 g of soybean protein (Essanmeat; trade name, produced by Ajinomoto Co., Ltd.), 1 g of dipotassium hydrogenphosphate and 0.2 g of magnesium sulfate heptahydrate were dissolved in 500 ml of purified water. Separately, 50 g of cholic acid, 5 g of sodium hydroxide and 2 g of sodium carbonate were dissolved in 500 ml of purified water. Both solutions were sterilized at 121° C. for 15 minutes and, after cooling, were mixed to give a medium (pH 10.2).

Thereafter, the procedure of Example 18 was repeated. The production ratio was 0% of cholic acid, 99.5% of 3α-hydroxy-7,12-diketo- 5β-cholanic acid, 0.3% of 3α, 12α-dihydroxy-7-keto-5β-cholanic acid and 0.2% of 3α, 7α-dihydroxy-12-keto-5β-cholanic acid.

EXAMPLE 25

The procedure of Example 24 was repeated except that Bacillus sp. TTUR 2-M4-250 was used as a strain. The production ratio was 0.5% of cholic acid and 99.5% of 3α, 12α-dihydroxy-7-keto-5β-cholanic acid.

EXAMPLE 26

Bacillus sp. TTUR 2-M4 was cultured by the following method. 10 g of glucose, 5 g of peptone, 5 g of yeast extract, 1 g of dipotassium hydrogenphosphate and 0.2 g of magnesium gulfate heptahydrate were dissolved in 500 ml of purified water. Separately, 100 g of cholic acid, 10 g of sodium hydroxide and 10 g of sodium carbonate were dissolved in 500 ml of purified water. Both solutions were sterilized at 121° C. for 15 minutes, and, after cooling, were mixed to give a medium (pH 10 ).

20 ml of this medium was put in a test tube (3Φ×19 cm), and 0.1 ml of a culture broth was aseptically inoculated therein which had been obtained by culturing the strain at 30° C. 24 hours in 20 ml of a medium having the same composition as above in a test tube. Then, shaking culture was carried out at 30° C. for 4 days.

Thereafter, the procedure of Example 19 was repeated. The production ratio was 2.0% of cholic acid, 74.0% of 30α-hydroxy-7,12-diketo- 5β-cholanic acid, 12.8% of 3α, 12α-dihydroxy-7-keto-5β-cholanic acid and 11.2% of 3α, 7α-dihydroxy-12-keto-5β-cholanic acid.

EXAMPLE 27

The procedure of Example 26 was repeated except that Bacillus sp. TTUR 2-M4-250 was used as a strain. The production ratio was 5.0% of cholic acid and 95.0% of 3α, 12α-dihydroxy-7-keto-5β-cholanic acid.

EXAMPLE 28

Bacillus sp. TTUR 2-M5 was cultured by the following method 10 g of soybean protein (Ajipron E3), 1 g of yeast extract, 2 g of dipotassium hydrogenphosphate and 0.4 g of magnesium gulfate heptahydrate were dissolved in 1000 ml of purified water. Separately, 100 g of chenodeoxycholic acid, 10 of sodium hydroxide and 5 g of sodium carbonate were dissolved in 1000 ml of purified water. Both solutions were mixed, without sterilization, in a 5-liter bench jar fermenter to give a medium (pH 10.4).

40 ml of a culture broth of Bacillus sp. TTUR 2-M5 was inoculated therein which had been obtained by culturing the strain with shaking at 3° C. for 20 hours in 20 ml of a medium in a test tube having the same composition as in the above medium except that chenodeoxycholic acid and sodium hydroxide were excluded. Thereafter, culture was carried out at 30° C. for 3 days with an aeration of 2 L/min and stirring (300 rpm).

After the culture, the cells were removed by centrifugation (3500 rpm×15 min) and the culture supernatant was adjusted to pH 2.5 with gulfuric acid to form a precipitate. This precipitate was filtered and washed with water, and the resultant crystalls were dried at 50° C. to give 99.2 g of white powder. Part of this was taken and subjected to high performance liquid chromatography. The thereby determined production ratio was 0% of chenodeoxycholic acid and 100% of 3α-hydroxy-7-keto-5β-cholanic acid (recovery 99.1% ).

EXAMPLE 29

The procedure of Example 28 was repeated except that Bacillus sp. TTUR 2-M4-250 was used as a strain. The production ratio was 0.5% of chenodeoxycholic acid and 99.5% of 3α-hydroxy-7-keto-5β-cholanic acid (recovery 99.0% ).

[Effect of the Invention]

By using novel microorganisms of the genus Bacillus according to this invention, a substrate chenodeoxycholic acid or cholic acid in a high concentration can be converted, in a high yield, to 3α-hydroxy-7-keto- 5β-cholanic acid, or 3α-hydroxy-7, 12-diketo-5β-cholanic acid or 3α, 12α-dihydroxy-7-keto- 5β-cholanic acid, each of which is a preparation intermediate for ursodeoxycholic acid.

TABLE 1

| Micro-organism | (1) Morphology | | |
| --- | --- | --- | --- |
| | Bacillus sp. TTUR 2-2 | Bacillus sp. TTUR 4-1 | Bacillus sp. TTUR 4-2 |
| Morphology | rod | rod | rod |

TABLE 1-continued

(1) Morphology

| Microorganism | Bacillus sp. TTUR 2-2 | Bacillus sp. TTUR 4-1 | Bacillus sp. TTUR 4-2 |
|---|---|---|---|
| Size (μm) | 0.4–0.7 × 1.5–4.5 | 0.4–0.7 × 1.5–4.5 | 0.4–0.7 × 1.5–4.5 |
| Cellular polymorphism | None (partially chained) | None (partially chained) | None (partially chained) |
| Flagellum | Peritrichous flagella | Peritrichous flagella | Peritrichous flagella |
| Spore | oval | oval | oval |
| Formation position | Slightly at the end of the cell | Slightly at the end of the cell | Slightly at the end of the cell |
| Sporangium | Slightly swelling | Slightly swelling | Slightly swelling |
| Size (μm) | 0.3–0.7 × 0.6–1.2 | 0.3–0.6 × 0.6–1.2 | 0.3–0.6 × 0.6–1.2 |
| Gram staining | Variable | Variable | Variable |
| Acid fastness | None | None | None |

TABLE 2

(2) Growth in various media
(All of the TTUR 2-2, TTUR 4-1 and TTUR 4-2 strains exhibited the following growth states)

| Kind of medium | Growth state pH 7.0 | pH 10.0 |
|---|---|---|
| ① Nutrient agar plate culture | Poor growth | Irregular, convex, and auriculate or lobate; milky-white and glistening |
| ② Nutrient agar slant culture | Poor growth | Grows in a spreading state. Pigment is not formed. |
| ③ Nutrient broth culture | Slight growth | Grows, slightly turbid. Sediment is observed. |
| ④ Gelatin stab culture | Not liquefied because of poor growth | Liquefies it stratiformly. |
| ⑤ Litmus milk | Change is scarcely observed | Grows and liquefies it. Litmus is not changed because of the alkaline environment. |

TABLE 3

Physical characteristics of the TTUR 2-2 strain (Part 1)

| | | |
|---|---|---|
| (1) Reduction of nitrate salt | Not or very weakly reduced | |
| (2) Denitrification | Not observed | |
| (3) MR test | Discoloration of methyl red is not observed because of the medium being alkaline | |
| (4) VP test | Negative | |
| (5) Formation of indole | Not formed | |
| (6) Formation of hydrogen sulfide | Not formed | |
| (7) Hydrolysis of starch | Hydrolized | |
| (8) Utilization of citric acid | | |
|    Koser citrate medium | Not utilized | |
|    Christensen agar | Excellently utilized | |
| (9) Utilization of inorganic nitrogen source | | |
|    Ammonium salt | Scarcely utilized | |
|    Nitrate salt | Scarcely utilized | |
| (10) Formation of pigment | Not formed | |
| (11) Urease (pH 9) | Negative | |

TABLE 3-continued

Physical characteristics of the TTUR 2-2 strain (Part 1)

| | |
|---|---|
| (12) Oxidase | Positive |
| (13) Catalase | Positive |
| (14) Range of growth | |
|    Growth pH | pH 7~11 (optimum pH 9~10) |
|    Growth temperature | 15~43° C. (optimum temperature 30~37° C.) |
| (15) Attitude to oxygen | Aerobic |
| (16) 0-F test | The strain grows in an aerobic condition, a slight amount of acid is formed, and formation of gas is not observed |
| (17) Resistance to sodium chloride | The strain grows in the presence of 10% sodium chloride but does not grow in the presence of 15% sodium chloride. |

TABLE 4

Physical characteristics of the TTUR 2-2 strain (Part 2)
(18) Formation of acid or gas from saccharides (pH 9)

| | Formation of acid | Formation of gas |
|---|---|---|
| L-arabinose | ± | − |
| D-xylose | ± | − |
| D-glucose | ± | − |
| D-mannose | − | − |
| D-fructose | + | − |
| D-galactose | − | − |
| Maltose | + | − |
| Sucrose | + | − |
| Lactose | − | − |
| Trehalose | + | − |
| D-sorbitol | − | − |
| D-mannitol | + | − |
| Inositol | − | − |
| Glycerol | − | − |
| Starch | + | − |

TABLE 5

Physical characteristics of the TTUR 4-1 strain (Part 1)

| | |
|---|---|
| (1) Reduction of nitrate salt | Reduced |
| (2) Denitrification | Not observed |
| (3) MR test | Discoloration of methyl red is not observed because of the medium being alkaline |
| (4) VP test | Negative |
| (5) Formation of indole | Not formed |
| (6) Formation of hydrogen sulfide | Not formed |
| (7) Hydrolysis of starch | Hydrolized |
| (8) Utilization of citric acid | |
|    Koser citrate medium | Not utilized |
|    Christensen agar | Excellently utilized |
| (9) Utilization of inorganic nitrogen source | |
|    Ammonium salt | Not utilized |
|    Nitrate salt | Not utilized |
| (10) Formation of pigment | Not formed |
| (11) Urease (pH 9) | Negative |
| (12) Oxidase | Positive |
| (13) Catalase | Positive |
| (14) Range of growth | |
|    Growth pH | pH 7~11 (optimum pH 9~10) |
|    Growth temperature | 15~40° C. (optimum |

TABLE 5-continued

Physical characteristics of the TTUR 4-1 strain (Part 1)

| | |
|---|---|
| (15) Attitude to oxygen | temperature 30~37° C.) Aerobic |
| (16) O-F test | The strain grows in an aerobic condition, a slight amount of acid is formed, and formation of gas is not observed |
| (17) Resistance to sodium chloride | The strain slightly grows in the presence of 15% sodium chloride. |

TABLE 6

Physical characteristics of the TTUR 4-1 strain (Part 2)
(18) Formation of acid or gas from saccharides (pH 9)

| | Formation of acid | Formation of gas |
|---|---|---|
| L-arabinose | − | − |
| D-xylose | + | − |
| D-glucose | − | − |
| D-mannose | − | − |
| D-fructose | + | − |
| D-galactose | − | − |
| Maltose | + | − |
| Sucrose | ± | − |
| Lactose | − | − |
| Trehalose | + | − |
| D-sorbitol | − | − |
| D-mannitol | + | − |
| Inositol | − | − |
| Glycerol | − | − |
| Starch | + | − |

TABLE 7

Physical characteristics of the TTUR 4-2 strain (Part 1)

| | |
|---|---|
| (1) Reduction of nitrate salt | Reduced |
| (2) Denitrification | Not observed |
| (3) MR test | Discoloration of methyl red is not observed because of the medium being alkaline |
| (4) VP test | Negative |
| (5) Formation of indole | Not formed |
| (6) Formation of hydrogen sulfide | Not formed |
| (7) Hydrolysis of starch | Hydrolized |
| (8) Utilization of citric acid | |
| Koser citrate medium | Not utilized |
| Christensen agar | Excellently utilized |
| (9) Utilization of inorganic nitrogen source | |
| Ammonium salt | Utilized |
| Nitrate salt | Scarcely utilized |
| (10) Formation of pigment | Not formed |
| (11) Urease (pH 9) | Negative |
| (12) Oxidase | Positive |
| (13) Catalase | Positive |
| (14) Range of growth | |
| Growth pH | pH 7~11 (optimum pH 9~10) |
| Growth temperature | 15~40° C. (optimum temperature 30~37° C.) |
| (15) Attitude to oxygen | Aerobic |
| (16) O-F test | The strain grows in an aerobic condition, a slight amount of acid is formed, and formation of gas is not observed |
| (17) Resistance to sodium chloride | The strain slightly grows in the presence of 15% sodium chloride. |

TABLE 8

Physical characteristics of the TTUR 4-2 strain (Part 2)
(18) Formation of acid or gas from saccharides (pH 9)

| | Formation of acid | Formation of gas |
|---|---|---|
| L-arabinose | ± | − |
| D-xylose | − | − |
| D-glucose | − | − |
| D-mannose | − | − |
| D-fructose | + | − |
| D-galactose | − | − |
| Maltose | + | − |
| Sucrose | − | − |
| Lactose | − | − |
| Trehalose | + | − |
| D-sorbitol | − | − |
| D-mannitol | + | − |
| Inositol | − | − |
| Glycerol | − | − |
| Starch | + | − |

TABLE 9

Main characteristics of each strain

| Microorganism | TTUR 2-2 | TTUR 4-1 | TTUR 4-2 |
|---|---|---|---|
| Shape of colonies | irregular | irregular | irregular |
| Periphery of colonies | auriculate | auriculate | auriculate |
| Color of colonies | milky-white | milky-white | milky-white |
| Liquefaction of gelatin | stratiform | stratiform | stratiform |
| Growth under an anaerobic environment | − | − | − |
| Growth temperature °C. | 15~43 | 15~40 | 15~40 |
| Optimum growth temperature °C. | 30~37 | 30~37 | 30~37 |
| Resistance to NaCl 15% | − | ± | ± |
| Utilization of NH$_4$ salt | − | − | ± |
| Reduction of nitrate salt | − | + | + |
| Utilization of citrate salt (Koser) | − | − | − |
| Formation of acid from saccharides | | | |
| L-arabinose | ± | − | ± |
| D-xylose | ± | + | − |
| D-glucose | ± | − | − |
| Sucrose | + | ± | − |

TABLE 10

Main characteristics of comparative strains

| Comparative strain | Bacillus alcalophilus | Bacillus alcalophilus subsp. halodurans | Bacillus cereus 8-1 (FERM P-2885) | Bacillus alcalophilus (FERM P-2674) |
|---|---|---|---|---|
| Shape of colonies | circular | circular | irregular | irregular |

TABLE 10-continued

Main characteristics of comparative strains

| Comparative strain | Bacillus alcalophilus | Bacillus alcalophilus subsp. halodurans | Bacillus cereus 8-1 (FERM P-2885) | Bacillus alcalophilus (FERM P-2674) |
|---|---|---|---|---|
| Periphery of colonies | entire | entire | lobate | lobate |
| Color of colonies | milky-white | milky-white | pale yellow | milky-white |
| Liquefaction of gelatin | stratiform | crateriform | stratiform | |
| Growth under an anaerobic environment | − | + | − | + |
| Growth temperature °C. | ~46 | ~54 | ~45 | ~50 |
| Optimum growth temperature °C. | 33~35 | around 48 | 40~45 | 40~43 |
| Resistance to NaCl 15% | − | + | | |
| Utilization of NH$_4$ salt | | | − | ± |
| Reduction of nitrate salt | − | + | | |
| Utilization of citrate | − | | ± | + |
| Formation of acid from saccharides | | | | |
| L-arabinose | + | + | + | + |
| D-xylose | + | + | + | + |
| D-glucose | + | + | + | + |
| Sucrose | + | + | + | + |

TABLE 11

(1) Morphology
(All of the TTUR 2-2, TTUR 2-M4, TTUR 2-M5, TTUR 2-M4-250 and TTUR 2-M4-294 strains exhibited the following characteristics)

| | |
|---|---|
| Morphology | rod |
| Size (μm) | 0.4~0.7 × 1.5~4.5 |
| Cellular polymorphism | None (partially chained) |
| Flagellum | *Peritrichous flagella* |
| Spore | oval |
| Formatin position | Slightly at the end of the cell |
| Sporangium | Slightly swelling |
| Size (μm) | 0.3~0.7 × 0.6~1.2 |
| Gram staining | Variable |
| Acid fastness | None |

TABLE 12

(2) Growth in various media
Growth state

| Kind of medium | pH 7.0 | | pH 10.0 |
|---|---|---|---|
| | TTUR 2-2, TTUR 2-M4, TTUR 2-M5 | TTUR 2-M4-250 TTUR 2-M4-294 | TTUR 2-2, TTUR 2-M4, TTUR 2-M5, TTUR 2-M4-250, TTUR 2-M4-294 |
| Nutrient agar plate culture | Poor growth | No growth | Irregular, convex, and auriculate or lobate; milky-white and glistening |
| Nutrient agar slant culture | Poor growth | No growth | Grows in a spreading state Pigment is not formed. |
| Nutrient broth culture | Slight growth | No growth | Grows, slightly turbid. Sediment is observed. |
| Gelatin stab culture | Not liquefied because of poor growth | No growth | Liquefies it stratiformly. |
| Litmus milk | Change is scarcely observed | No growth | Grows and liquefies it. Litmus is not changed because of the alkaline environment. |

TABLE 13

Physical characteristics
(All of the TTUR 2-2, TTUR 2-M4, TTUR 2-M5, TTUR 2-M4-250, and TTUR 2-M4-294 strains exhibited the following characteristics)

| | |
|---|---|
| Reduction of nitrate salt | Not or very weakly reduced |
| Denitrification | Not observed |
| MR test | Discoloration of methyl red is not observed because of the |

TABLE 13-continued

Physical characteristics
(All of the TTUR 2-2, TTUR 2-M4, TTUR 2-M5,
TTUR 2-M4-250, and TTUR 2-M4-294 strains exhibited the
following characteristics)

| | | |
|---|---|---|
| VP test | | medium being alkaline Negative |
| Formation of indole | | Not formed |
| Formation of hydrogen sulfide | | Not formed |
| Hydrolysis of starch | | Hydrolized |
| Utilization of citric acid | | |
| Koser citrate medium | | Not utilized |
| Christensen agar | | Excellently utilized |
| Utilization of inorganic nitrogen source | | |
| Ammonium salt | | Scarcely utilized |
| Nitrate salt | | Scarcely utilized |
| Formation of pigment | | Not formed |
| Urease (pH 9) | | Negative |
| Oxidase | | Positive |
| Catalase | | Positive |
| Range of growth | | |
| TTUR 2-2 | Growth pH | pH 7~11 (optimum pH 9~10) |
| TTUR 2-M4 TTUR 2-M5 | Growth temperature | 15~43° C. (optimum temperature 30~37° C.) |
| TTUR 2-M4-250 | Growth pH | pH 7.3~11 (optimum pH 9~10) |
| TTUR 2-M4-294 | Growth temperature | 15~40° C. (optimum temperature 30~37° C.) |
| Attitude to oxygen | | Aerobic |
| O-F test | | The strain grows in an aerobic condition, a slight amount of acid is formed, and formation of gas is not observed |
| Resistance to sodium chloride | | The strain grows in the presence of 10% sodium chloride but does not grow in the presence of 15% sodium chloride. |

TABLE 14

Formation of acid or gas from saccharides (pH 9)
Bacillus sp. TTUR 2-2

| Saccharide | Formation of acid | Formation of gas |
|---|---|---|
| L-arabinose | ± | − |
| D-xylose | ± | − |
| D-glucose | ± | − |
| D-mannose | − | − |
| D-fructose | + | − |
| D-galactose | − | − |
| Maltose | + | − |
| Sucrose | + | − |
| Lactose | − | − |
| Trehalose | + | − |
| D-sorbitol | − | − |
| D-mannitol | + | − |
| Inositol | − | − |
| Glycerol | − | − |
| Starch | + | − |

TABLE 15

Formation of acid or gas from saccharides (pH 9)
Bacillus sp. TTUR 2-M4

| Saccharide | Formation of acid | Formation of gas |
|---|---|---|
| L-arabinose | ± | − |

TABLE 15-continued

Formation of acid or gas from saccharides (pH 9)
Bacillus sp. TTUR 2-M4

| Saccharide | Formation of acid | Formation of gas |
|---|---|---|
| D-xylose | − | − |
| D-glucose | ± | − |
| D-mannose | − | − |
| D-fructose | + | − |
| D-galactose | − | − |
| Maltose | + | − |
| Sucrose | + | − |
| Lactose | − | − |
| Trehalose | + | − |
| D-sorbitol | − | − |
| D-mannitol | + | − |
| Inositol | − | − |
| Glycerol | − | − |
| Starch | + | − |

TABLE 16

Formation of acid or gas from saccharides (pH 9)
Bacillus sp. TTUR 2-M5

| Saccharide | Formation of acid | Formation of gas |
|---|---|---|
| L-arabinose | + | − |
| D-xylose | + | − |
| D-glucose | + | − |
| D-mannose | − | − |
| D-fructose | + | − |
| D-galactose | − | − |
| Maltose | ± | − |
| Sucrose | ± | − |
| Lactose | − | − |
| Trehalose | + | − |
| D-sorbitol | − | − |
| D-mannitol | + | − |
| Inositol | − | − |
| Glycerol | − | − |
| Starch | ± | − |

TABLE 17

Formation of acid or gas from saccharides (pH 9)
Bacillus sp. TTUR 2-M4-250

| Saccharide | Formation of acid | Formation of gas |
|---|---|---|
| L-arabinose | ± | − |
| D-xylose | − | − |
| D-glucose | + | − |
| D-mannose | − | − |
| D-fructose | + | − |
| D-galactose | − | − |
| Maltose | + | − |
| Sucrose | ± | − |
| Lactose | − | − |
| Trehalose | + | − |
| D-sorbitol | − | − |
| D-mannitol | − | − |
| Inositol | − | − |
| Glycerol | − | − |
| Starch | ± | − |

TABLE 18

Formation of acid or gas from saccharides (pH 9)
Bacillus sp. TTUR 2-M4-294

| Saccharide | Formation of acid | Formation of gas |
|---|---|---|
| L-arabinose | ± | − |

TABLE 18-continued

Formation of acid or gas from saccharides (pH 9)
Bacillus sp. TTUR 2-M4-294

| Saccharide | Formation of acid | Formation of gas |
| --- | --- | --- |
| D-xylose | − | − |
| D-glucose | + | − |
| D-mannose | − | − |
| D-fructose | + | − |
| D-galactose | − | − |
| Maltose | + | − |
| Sucrose | ± | − |
| Lactose | − | − |
| Trehalose | + | − |
| D-sorbitol | − | − |
| D-mannitol | + | − |
| Inositol | − | − |
| Glycerol | − | − |
| Starch | + | − |

TABLE 19

Main characteristics of each strain (Part 1)

| Microorganism | Bacillus sp. TTUR 2-2 | Bacillus sp. TTUR 2-M4 | Bacillus sp. TTUR 2-M5 |
| --- | --- | --- | --- |
| Shape of colonies | irregular | irregular | irregular |
| Periphery of colonies | auriculate | auriculate | auriculate |
| Color of colonies | milky-white | milky-white | milky-white |
| Liquefaction of gelatin | stratiform | stratiform | stratiform |
| Growth under an anaerobic environment | − | − | − |
| Growth temperature °C. | 15–43° C. | 15–43° C. | 15–43° C. |
| Optimum growth temperature °C. | 30–37° C. | 30–37° C. | 30–37° C. |
| Resistance to NaCl 15% | − | − | − |
| Utilization of NH$_4$ salt | − | − | − |
| Reduction of nitrate salt | − | − | − |
| Utilization of citrate salt (Koser) | − | − | − |
| Formation of acid from saccharides | | | |
| L-arabinose | ± | ± | + |
| D-xylose | ± | − | + |
| D-glucose | ± | ± | + |
| Sucrose | + | + | ± |

TABLE 20

Main characteristics of each strain (Part 2)

| Microorganism | Bacillus sp. TTUR 2-M4-250 | Bacillus sp. TTUR 2-M4-294 |
| --- | --- | --- |
| Shape of colonies | irregular | irregular |
| Periphery of colonies | auriculate | auriculate |
| Color of colonies | milky-white | milky-white |
| Liquefaction of gelatin | stratiform | stratiform |
| Growth under an anaerobic environment | − | − |
| Growth temperature °C. | 15–40° C. | 15–40° C. |
| Optimum growth temperature °C. | 30–37° C. | 30–37° C. |
| Resistance to NaCl 15% | − | − |
| Utilization of NH$_4$ salt | − | − |
| Reduction of nitrate salt | − | − |
| Utilization of citrate salt (Koser) | − | − |
| Formation of acid from saccharides | | |
| L-srabinose | ± | ± |
| D-xylose | − | − |
| D-glucose | + | + |
| Sucrose | ± | ± |

What is claimed is:

1. A biologically pure culture of a Bacillus selected from the group consisting of Bacillus FERM BP-4390, Bacillus FERM BP 4391, Bacillus FERM BP-3651, Bacillus FERM BP-3393, Bacillus FERM BP-3398, Bacillus FERM BP-3395 and Bacillus FERM BP-3396.

2. Process for producing 3 alpha-hydroxy-7-keto-5beta-cholanic acid from chenodeoxycholic acid, which comprises culturing a microorganism belonging to the genus Bacillus and having an ability to convert chenodeoxycholic acid to 3alpha-hydroxy- 7-keto-5beta-cholanic acid under aerobic conditions at alkaline pH, in a nutrient medium containing chenodeoxycholic acid under aerobic conditions at alkaline pH, and recovering the thereby produced 3alpha-hydroxy-7-keto-5beta-cholanic acid from the resulting culture broth, wherein said microorganism is selected from the group consisting of Bacillus sp. FERM BP-3651, Bacillus sp. FERM BP-4390, Bacillus sp. FERM BP-4391, Bacillus sp. FERM BP-3393, Bacillus sp. FERM BP-3398, Bacillus sp. FERM BP-3395 and Bacillus sp. FERM BP-3396.

3. Process of claim 2 wherein the pH of the nutrient medium is an alkaline pH up to 11, and the chenodeoxycholic acid is present in a concentration of about 5 to 500 g/L.

4. Process for producing 3alpha-hydroxy-7, 12-diketo-5-beta-cholanic acid from cholic acid, which comprises culturing an alkalophilic microorganism belonging to the genus alkalophilic Bacillus and having an ability to convert cholic acid to 3alpha-hydroxy- 7,12-diketo-5beta-cholanic acid under aerobic conditions at alkaline pH, in a nutrient medium containing cholic acid under aerobic conditions at alkaline pH, and recovering the thereby produced 3 alpha-hydroxy-7,12-diketo-5 beta-cholanic acid from the resulting culture broth, wherein said microorganism is selected from the group consisting of Bacillus sp. FERM BP-3393 and Bacillus sp. FERM BP-3398.

5. Process of claim 4 wherein the pH of the nutrient medium is an alkaline pH up to 11, and the cholic acid is present in a concentration of about 5 to 500 g/L.

6. Process for producing 3 alpha, 12 alpha-dihydroxy-7-keto-5 beta-cholanic acid from cholic acid, which comprises culturing an alkalophilic microorganism belonging to the genus alkalophilic Bacillus and having an ability to convert cholic acid to 3 alpha, 12 alpha-hydroxy-7-keto-5 beta-cholanic acid under aerobic conditions at alkaline pH, in a nutrient medium containing cholic acid under aerobic conditions at alkaline pH, and recovering the thereby produced 3 alpha, 12 alpha-dihydroxy- 7-keto-5 beta-cholanic acid from the resulting culture broth, wherein said microorganism is selected from the group consisting of Bacillus sp. FERM BP-3395 and Bacillus sp. FERM BP-4390.

7. Process of claim 6 wherein the pH of the nutrient medium is an alkaline pH up to 11, and the cholic acid is present in a concentration of about 5 to 500 g/L.

* * * * *